(12) United States Patent
Hulse et al.

(10) Patent No.: US 8,518,293 B2
(45) Date of Patent: Aug. 27, 2013

(54) 1,3,3,3-TETRAFLUOROPROPENE PROCESS AZEOTROPES WITH HF

(75) Inventors: Ryan Hulse, Getzville, NY (US); Hang T. Pham, Amherst, NY (US); Rajiv Ratna Singh, Getzville, NY (US); Daniel C Merkel, Orchard Park, NY (US); Konstantin A. Pokrovski, Orchard Park, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 384 days.

(21) Appl. No.: 12/875,181

(22) Filed: Sep. 3, 2010

(65) Prior Publication Data

US 2012/0056122 A1    Mar. 8, 2012

(51) Int. Cl.
*C09K 5/04*    (2006.01)

(52) U.S. Cl.
USPC ............. 252/67; 510/177; 510/408; 510/410; 510/415

(58) Field of Classification Search
USPC .................... 252/67; 510/177, 408, 410, 415
See application file for complete search history.

(56) References Cited

U.S. PATENT DOCUMENTS

| | | | |
|---|---|---|---|
| 5,811,603 A | | 9/1998 | Elsheikh |
| 6,001,796 A * | | 12/1999 | Pham et al. .................. 510/408 |
| 6,472,573 B1 | | 10/2002 | Yamamoto |
| 7,423,188 B2 | | 9/2008 | Miller et al. |
| 7,485,760 B2 | | 2/2009 | Wang et al. |
| 2006/0106263 A1 | | 5/2006 | Miller et al. |
| 2007/0100173 A1 | | 5/2007 | Miller et al. |
| 2008/0051612 A1 | | 2/2008 | Knapp et al. |
| 2008/0207963 A1 | | 8/2008 | Rao et al. |
| 2009/0127496 A1 * | | 5/2009 | Rao et al. ................ 252/67 |
| 2010/0016457 A1 | | 1/2010 | Bowman et al. |
| 2010/0048961 A1 | | 2/2010 | Merkel et al. |
| 2010/0072415 A1 | | 3/2010 | Rao et al. |
| 2010/0200798 A1 * | | 8/2010 | Rao et al. ................ 252/67 |

FOREIGN PATENT DOCUMENTS

| | | |
|---|---|---|
| WO | 2008012559 A1 | 1/2008 |
| WO | 2009105512 A1 | 8/2009 |
| WO | 2009105521 A1 | 8/2009 |

OTHER PUBLICATIONS

PCT Search Report & Written Opinion dated—Apr. 13, 2012.
Kim et al. ; (Mar. 1996) "A Study to Determine the Existence of an Azeotropic R-22 "Drop-In" Substitute"; Source: Report from the Building Environment Division of the Building & Fire Research Laboratory of the U.S. Department of Commerce.
G. Morrison & M.O. McLinden ; (1993) "Azeotropy in refrigerant mixtures"; Source: International Journal of Refrigeration, vol. 16, No. 2, pp. 129-138.

* cited by examiner

*Primary Examiner* — Douglas McGinty
(74) *Attorney, Agent, or Firm* — Bruce O. Bradford

(57) ABSTRACT

The present invention pertains to azeotropic and azeotrope-like compositions of the following three blends:
1. Trans-1,3,3,3-tetrafluoropropene (HFO-1234ze(E)), cis-1,3,3,3-tetrafluoropropene (HFO-1234ze(Z)) and hydrogen fluoride (HF);
2. HFO-1234ze(E), 1,1,1,3,3-pentafluoropropane (HFC-245fa) and HF; and
3. HFO-1234ze(Z), HFC-245fa and HF.

These azeotropic and azeotrope-like compositions are useful as intermediates in the production of HFO-1234ze(E).

22 Claims, No Drawings

1,3,3,3-TETRAFLUOROPROPENE PROCESS AZEOTROPES WITH HF

FIELD OF THE INVENTION

The present invention pertains to azeotropic and azeotrope-like compositions of the following three blends:
1. Trans-1,3,3,3-tetrafluoropropene (HFO-1234ze(E)), cis-1,3,3,3-tetrafluoropropene (HFO-1234ze(Z)) and hydrogen fluoride (HF);
2. HFO-1234ze(E), 1,1,1,3,3-pentafluoropropane (HFC-245fa) and HF; and
3. HFO-1234ze(Z), HFC-245fa and HF.

More particularly the invention pertains to such azeotropic and azeotrope-like compositions which are useful as intermediates in the production of HFO-1234ze(E).

BACKGROUND OF THE INVENTION

Traditionally, chlorofluorocarbons (CFCs) like trichlorofluoromethane and dichlorodifluoromethane have been used as refrigerants, blowing agents and diluents for gaseous sterilization. In recent years there has been universal concern that completely halogenated chlorofluorocarbons might be detrimental to the earth's ozone layer. Therefore, stratospherically safer alternatives to these materials are desirable. Consequently, there is a worldwide effort to use fluorine-substituted hydrocarbons which contain fewer or no chlorine substituents. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are non-flammable, and non-toxic as compared to the chlorine containing compounds.

HFO-1234ze(E) is also known as trans-1,3,3,3-tetrafluoropropene, which is Honeywell's new low global warming potential (GWP), fourth generation blowing agent and propellant. This low GWP molecule is the first hydrofluoroolefin (HFO) to be commercialized into these industries. This molecule has low environmental impact, as measured by its ultralow global warming potential and zero ozone depletion potential (ODP). HFO-1234ze(E) blowing agent is fully compliant with the European Union's F-Gas regulation. As a gas material at room temperature, this molecule has diverse applications including as a blowing agent for polyurethanes, polystyrene and other polymers; as well as an aerosol propellant.

US Patent Publication No. 20080051611 provides a process in which 1,1,1,3,3-pentafluoropropane (HFC-245fa) is converted into trans-1,3,3,3-tetrafluoropropene (HFO-1234ze(E)). The HFC-245fa is dehydrofluorinated to produce a mixture of HFO-1234ze(E), cis-1,3,3,3-tetrafluoropropene (HFO-1234ze(Z)), HFC-245fa and hydrogen fluoride (HF). HFO-1234ze(E) has been disclosed as a useful blowing agent in one component foams.

It has now been found that an important intermediate in the production of substantially pure HFO-1234ze(E), are the azeotropic or azeotrope-like compositions of HFO-1234ze(E)/HFO-1234ze(Z)/HF, HFO-1234ze(E)/HFC-245fa/HF and HFO-1234ze(Z)/HFC-245fa/HF. These intermediates, once formed, may thereafter be separated into its component parts by known extraction techniques. The azeotropic and azeotrope-like compositions find use not only as intermediates in the production of HFO-1234ze(E), but they are additionally useful as nonaqueous etchant mixtures for etching semiconductors in the electronics industry, as well as compositions for removing surface oxidation from metals. These ternary azeotrope or azeotrope-like compositions are then available for separation into their component parts.

SUMMARY OF THE INVENTION

The invention provides an azeotropic or azeotrope-like compositions consisting essentially one of the three following blends:
1. HFO-1234ze(E), HFO-1234ze(Z) and HF;
2. HFO-1234ze(E), HFC-245fa, HF; and
3. HFO-1234ze(Z), HFC-245fa and HF.

The invention further provides a method of forming an azeotropic or azeotrope-like composition which comprises forming a blend consisting essentially of from about 1 to about 30 weight percent hydrogen fluoride, about 1 to 30 weight percent HFO-1234ze(Z) and from about 50 to about 99 weight percent HFO-1234ze(E) to thereby form an azeotropic or azeotrope-like composition having a boiling point of from about 0° C. to about 60° C. at a pressure of from about 30 psia to about 211 psia.

The invention also provides a method of forming an azeotropic or azeotrope-like composition which comprises forming a blend consisting essentially of from about 1 to about 30 weight percent hydrogen fluoride, about 10 to 70 weight percent HFO-1234ze(E) and from about 10 to about 60 weight percent HFC-245fa to thereby form an azeotropic or azeotrope-like composition having a boiling point of from about 0° C. to about 60° C. at a pressure of from about 24 psia to about 175 psia.

The invention also provides a method of forming an azeotropic or azeotrope-like composition which comprises forming a blend consisting essentially of from about 1 to about 30 weight percent hydrogen fluoride, about 20 to 80 weight percent HFO-1234ze(Z) and from about 10 to about 60 weight percent HFC-245fa to thereby form an azeotropic or azeotrope-like composition having a boiling point of from about 0° C. to about 60° C. at a pressure of from about 9 psia to about 105 psia.

The invention also provides a method for removing for purifying HFO-1234ze(E), HFO-1234ze(Z) and/or HFC-245fa or a mixture thereof from the previously mentioned azeotropes by first extracting HF from the azeotrope using sulfuric acid, water and/or a basic solution such as aqueous caustic solution to extract or react with the HF. The remaining binary or ternary mixtures of HFO-1234ze(E), HFO-1234ze(Z) and HFC-245fa can then be separated into the pure components by distillation or other commonly used separation techniques.

DETAILED DESCRIPTION OF THE INVENTION

HFO-1234ze(E)/HFO-1234ze(Z), HFO-1234ze(E)/HFC-245fa and HFO-1234ze(Z)/HFC-245fa form azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions.

An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling.

For the purpose of this invention, azeotropic compositions are defined to include azeotrope-like compositions, namely a composition that behaves like an azeotrope, i.e., has constant-boiling characteristics, or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

The essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of HFO-1234ze(E)/HFO-1234ze(Z), HFO-1234ze(E)/HFC-245fa, HFO-1234ze(Z)/HFC-245fa and HF to form an azeotropic or azeotrope-like composition. By effective amount is meant an amount of each component which, when combined with the other component, results in the formation of an azeotrope or azeotrope-like mixture. The inventive compositions preferably are ternary azeotropes which consist essentially of combinations of HFO-1234ze(E)/HFO-1234ze(Z), HFO-1234ze(E)/HFC-245 fa, HFO-1234ze(Z)/HFC-245fa and HF.

The invention also provides a method of forming an azeotropic or azeotrope-like composition which comprises forming a blend consisting essentially of from about 1 to about 30 weight percent hydrogen fluoride, about 10 to 70 weight percent HFO-1234ze(E) and from about 10 to about 60 weight percent HFC-245fa to thereby form an azeotropic or azeotrope-like composition having a boiling point of from about 0° C. to about 60° C. at a pressure of from about 25 psia to about 180 psia.

The invention also provides a method of forming an azeotropic or azeotrope-like composition which comprises forming a blend consisting essentially of from about 1 to about 30 weight percent hydrogen fluoride, about 20 to 80 weight percent HFO-1234ze(Z) and from about 10 to about 60 weight percent HFC-245fa to thereby form an azeotropic or azeotrope-like composition having a boiling point of from about 0° C. to about 60° C. at a pressure of from about 9 psia to about 105 psia.

In a preferred embodiment, the inventive composition contains from about 1 to about 30 weight percent HF and from about 1 to about 30 weight HFO-1234ze(Z) and 50 to about 99 wt % HFO-1234ze(E) based on the weight of the azeotropic or azeotrope-like composition. In which the composition of the present invention preferably has a boiling point of about from 0° C. to about 60° C. at a pressure of about 30 psia to about 211 psia. In one embodiment it has a boiling point of about 0° C. at a pressure of about 35±5 psia. In another embodiment it has a boiling point of about 25° C. at a pressure of about 81±5 psia. In another embodiment it has a boiling point of about 60° C. at a pressure of about 206±5 psia.

In a preferred embodiment, the inventive composition contains from about 1 to about 30 weight percent HF and from about 10 to about 70 weight HFO-1234ze(E) and 10 to about 60 wt % HFC-245fa based on the weight of the azeotropic or azeotrope-like composition. In which the composition of the present invention preferably has a boiling point of about from 0° C. to about 60° C. at a pressure of about 24 psia to about 175 psia. In one embodiment it has a boiling point of about 0° C. at a pressure of about 28±4 psia. In another embodiment it has a boiling point of about 25° C. at a pressure of about 65±5 psia. In another embodiment it has a boiling point of about 60° C. at a pressure of about 170±5 psia.

In a preferred embodiment, the inventive composition contains from about 1 to about 30 weight percent HF and from about 20 to about 80 weight HFO-1234ze(Z) and 10 to about 60 wt % HFC-245fa based on the weight of the azeotropic or azeotrope-like composition. In which the composition of the present invention preferably has a boiling point of about from 0° C. to about 60° C. at a pressure of about 9 psia to about 105 psia. In one embodiment it has a boiling point of about 0° C. at a pressure of about 13±4 psia. In another embodiment it has a boiling point of about 25° C. at a pressure of about 35±5 psia. In another embodiment it has a boiling point of about 60° C. at a pressure of about 100±5 psia.

The following non-limiting examples serve to illustrate the invention.

EXAMPLE 1

A mixture of 98.4 wt % HFO-1234ze(E) and 1.6 wt % HFO-1234ze(Z) was prepared. The pressure of the mixture was measures at temperatures near 0° C., 25° C. and 60° C. HF was incrementally added and the pressures at temperatures of 0° C., 25° C. and 60° C. of the ternary mixtures were measured and are shown in Table 1. The data in Table 1 show that as the concentration of HF is increased the pressure rises and then levels out which indicated the formation of a heterogeneous azeotrope like mixture. A vapor sample from the final concentration of the heterogeneous azeotrope and was analyzed to show that the azeotropic concentration was 3.3 wt % HF.

TABLE 1

PTx measurements of HFO-1234ze(E), HFO-1234ze(Z) and HF

| HF, wt % | Temp, ° C. | Press, psia |
|---|---|---|
| 0.00 | 0.0 | 31.0 |
| 0.00 | 24.9 | 71.3 |
| 0.00 | 59.8 | 179.2 |
| 5.98 | 0.0 | 35.0 |
| 5.98 | 24.9 | 81.1 |
| 5.98 | 59.8 | 207.2 |
| 10.6 | 0.0 | 35.0 |
| 10.6 | 24.9 | 81.1 |

TABLE 1-continued

PTx measurements of HFO-1234ze(E), HFO-1234ze(Z) and HF

| HF, wt % | Temp, ° C. | Press, psia |
|---|---|---|
| 10.6 | 59.8 | 206.2 |
| 21.89 | 0.0 | 34.9 |
| 21.89 | 24.9 | 80.4 |
| 21.89 | 59.8 | 204.3 |

EXAMPLE 2

A mixture of 65.33 wt % HFO-1234ze(E) and 34.67 wt % HFC-245fa was prepared. The pressure of the mixture was measures at temperatures near 0° C., 25° C. and 60° C. HF was incrementally added and the pressures at temperatures of 0° C., 25° C. and 60° C. of the ternary mixtures were measured and are shown in Table 2. The data in Table 2 show that as the concentration of HF is increased the pressure rises and then levels out which indicated the formation of a heterogeneous azeotrope like mixture. A vapor sample from the final concentration of the heterogeneous azeotrope and was analyzed to show that the azeotropic concentration was 4.97 wt % HF.

TABLE 2

HFO-1234ze(E), 1,1,1,3,3-pentafluoropropane (HFC-245fa), HF

| HF, wt % | Temp, ° C. | Press, psia |
|---|---|---|
| 0 | 0.0 | 24.3 |
| 0 | 24.9 | 56.1 |
| 0 | 59.8 | 143.2 |
| 5.8 | 0.0 | 28.2 |
| 5.8 | 24.9 | 66.1 |
| 5.8 | 59.8 | 172.1 |
| 18.1 | 0.0 | 28.2 |
| 18.1 | 24.9 | 66.0 |
| 18.1 | 59.8 | 170.8 |

EXAMPLE 3

A mixture of 60.9 wt % HFO-1234ze(Z) and 39.1 wt % HFC-245fa was prepared. The pressure of the mixture was measures at temperatures near 0° C., 25° C. and 60° C. HF was incrementally added and the pressures at temperatures of 0° C., 25° C. and 60° C. of the ternary mixtures were measured and are shown in Table 3. The data in Table 3 show that as the concentration of HF is increased the pressure rises and then levels out which indicated the formation of a heterogeneous azeotrope like mixture. A vapor sample from the final concentration of the heterogeneous azeotrope and was analyzed to show that the azeotropic concentration was 12.45 wt % HF.

TABLE 3

HFO-1234ze(Z), HFC-245fa and HF

| HF, wt % | Temp, ° C. | Press, psia |
|---|---|---|
| 0 | 0.0 | 9.3 |
| 0 | 24.9 | 24.5 |
| 0 | 59.8 | 71.4 |
| 7.16 | 0.0 | 13.5 |
| 7.16 | 24.9 | 34.6 |
| 7.16 | 59.8 | 100.9 |
| 13.41 | 0.0 | 13.7 |
| 13.41 | 24.9 | 35.2 |
| 13.41 | 59.8 | 100.5 |
| 17.33 | 0.0 | 13.7 |
| 17.33 | 24.9 | 35.3 |
| 17.33 | 59.8 | 100.8 |

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. An azeotrope or azeotrope-like composition consisting essentially of from about 1 to about 30 weight percent hydrogen fluoride, about 1 to 30 weight percent HFO-1234ze(Z) and from about 50 to about 99 weight percent HFO-1234ze(E), and having a boiling point of from about 0° C. to about 60° C. at a pressure of from about 30 psia to about 211 psia.

2. The composition of claim 1, having a boiling point of about 0° C. at a pressure of about 35±5 psia.

3. The composition of claim 1, having a boiling point of about 25° C. at a pressure of about 81±5 psia.

4. The composition of claim 1, having a boiling point of about 60° C. at a pressure of about 206±5 psia.

5. An azeotrope or azeotrope-like composition consisting essentially of from about 1 to about 30 weight percent hydrogen fluoride, about 20 to 80 weight percent HFO-1234ze(Z) and from about 10 to about 60 weight percent HFC-245fa, and having a boiling point of from about 0° C. to about 60° C. at a pressure of from about 9 psia to about 105 psia.

6. The composition of claim 5, having a boiling point of about 0° C. at a pressure of about 13±4 psia.

7. The composition of claim 5, having a boiling point of about 25° C. at a pressure of about 35±5 psia.

8. The composition of claim 5, having a boiling point of about 60° C. at a pressure of about 100±5 psia.

9. A method of forming an azeotropic or azeotrope-like composition which comprises forming a blend consisting essentially of from about 1 to about 30 weight percent hydrogen fluoride, about 1 to 30 weight percent HFO-1234ze(Z) and from about 50 to about 99 weight percent HFO-1234ze(E) to thereby form an azeotropic or azeotrope-like composition having a boiling point of from about 0° C. to about 60° C. at a pressure of from about 30 psia to about 211 psia.

10. A method of forming an azeotropic or azeotrope-like composition which comprises forming a blend consisting essentially of from about 1 to about 30 weight percent hydrogen fluoride, about 20 to 80 weight percent HFO-1234ze(Z) and from about 10 to about 60 weight percent HFC-245fa to thereby form an azeotropic or azeotrope-like composition having a boiling point of from about 0° C. to about 60° C. at a pressure of from about 9 psia to about 105 psia.

11. A method of separating the composition of claim 1 comprising swing distillation of the composition.

12. The method of claim 11, further comprising an initial step of removing the HF from the composition.

13. The method of claim 12, wherein the HF removal is accomplished by scrubbing with sulfuric acid, water and/or a basic solution.

14. A method of separating the composition of claim 1 comprising, extractive distillation.

15. The method of claim 14, further comprising an initial step of removing the HF from the composition.

16. The method of claim 15, wherein the HF removal is accomplished by scrubbing with sulfuric acid, water and/or a basic solution.

17. A method of separating the composition of claim 5 comprising swing distillation of the composition.

18. The method of claim 17, further comprising an initial step of removing the HF from the composition.

19. The method of claim 18, wherein the HF removal is accomplished by scrubbing with sulfuric acid, water and/or a basic solution.

20. A method of separating the composition of claim 5 comprising, extractive distillation.

21. The method of claim 20, further comprising an initial step of removing the HF from the composition.

22. The method of claim 21, wherein the HF removal is accomplished by scrubbing with sulfuric acid, water and/or a basic solution.

* * * * *